US012082831B2

(12) United States Patent
Novak

(10) Patent No.: US 12,082,831 B2
(45) Date of Patent: Sep. 10, 2024

(54) COMBINED SHOCKWAVE AND ULTRASOUND SOURCE

(71) Applicant: Storz Medical AG, Tägerwilen (CH)

(72) Inventor: Pavel Novak, Stetten (CH)

(73) Assignee: STORZ MEDICAL AG (CH)

(*) Notice: Subject to any disclaimer, the term of this patent is extended or adjusted under 35 U.S.C. 154(b) by 579 days.

(21) Appl. No.: 17/373,203

(22) Filed: Jul. 12, 2021

(65) Prior Publication Data
US 2021/0338259 A1 Nov. 4, 2021

Related U.S. Application Data

(63) Continuation of application No. PCT/EP2020/051146, filed on Jan. 17, 2020.

(30) Foreign Application Priority Data

Jan. 18, 2019 (EP) ..................................... 19152500

(51) Int. Cl.
*A61B 17/225* (2006.01)
(52) U.S. Cl.
CPC ................................ *A61B 17/2256* (2013.01)
(58) Field of Classification Search
CPC .................................................. A61B 17/2256
See application file for complete search history.

(56) References Cited

U.S. PATENT DOCUMENTS

| 4,928,672 A | * | 5/1990 | Grasser | A61B 17/2258 601/4 |
| 4,976,255 A | | 12/1990 | Reichenberger | |
| 5,044,354 A | * | 9/1991 | Goldhorn | A61B 17/2255 601/4 |
| 5,058,569 A | * | 10/1991 | Hassler | G10K 9/12 601/4 |
| 5,174,280 A | * | 12/1992 | Gruenwald | G10K 15/043 367/175 |
| 5,228,447 A | * | 7/1993 | Harder | A61B 17/2258 601/4 |

(Continued)

FOREIGN PATENT DOCUMENTS

| CN | 108720897 A | 11/2018 | |
| DE | 102006021049 A1 * | 11/2007 | ......... A61B 17/2251 |

(Continued)

OTHER PUBLICATIONS

Adam et al., "Fragmentation of urinary calculi in vitro by burst wave lithotripsy", Jan. 2015, The Journal of Urology, vol. 193, pp. 338-344 (Year: 2015).*

(Continued)

*Primary Examiner* — Dixomara Vargas
(74) *Attorney, Agent, or Firm* — Quarles & Brady LLP; Yakov S. Sidorin

(57) ABSTRACT

An apparatus for generating focused shockwaves and ultrasound waves comprises a concave reflector holding a cylindrical coil at its center axis. A power generator comprising a combined shockwave and ultrasound generator device is connected to the coil for alternatingly providing an ultrasound signal and a shockwave signal to the coil such that the coil alternatingly generates ultrasound waves and shockwaves.

14 Claims, 4 Drawing Sheets

(56) References Cited

U.S. PATENT DOCUMENTS

| | | | | |
|---|---|---|---|---|
| 5,251,630 | A | * | 10/1993 | Rattner .................... G10K 9/12 367/175 |
| 5,374,236 | A | * | 12/1994 | Hassler .................... G10K 9/12 367/175 |
| 5,703,922 | A | * | 12/1997 | Rattner .............. A61B 17/2255 600/407 |
| 5,941,838 | A | | 8/1999 | Eizenhofer |
| 9,901,753 | B2 | * | 2/2018 | Cain .................... A61B 17/225 |
| 10,500,128 | B2 | * | 12/2019 | Engles ............... A61B 17/2251 |
| 2003/0161217 | A1 | * | 8/2003 | Rohwedder ........... B06B 1/0215 367/142 |
| 2010/0249671 | A1 | * | 9/2010 | Coleman .............. A61B 17/225 601/4 |
| 2011/0054363 | A1 | | 3/2011 | Cain |
| 2015/0231414 | A1 | * | 8/2015 | Ein-Gal ................. G10K 9/125 601/2 |
| 2021/0346533 | A1 | * | 11/2021 | Cioanta .................. A61B 90/70 |
| 2023/0248382 | A1 | * | 8/2023 | Storz .................. A61B 17/2255 600/427 |

FOREIGN PATENT DOCUMENTS

| | | | |
|---|---|---|---|
| EP | 0263349 | A1 | 4/1988 |
| EP | 1651120 | B1 | 5/2006 |
| EP | 2529678 | B1 | 12/2012 |
| JP | S62152447 | A | 12/1985 |
| JP | H01181858 | A | 7/1989 |
| JP | H0435657 | A | 2/1992 |
| JP | H06261907 | A | 9/1994 |
| JP | H0747078 | A | 2/1995 |
| JP | 2003093396 | A | 4/2003 |
| KR | 20090117208 | A | 11/2009 |

OTHER PUBLICATIONS

JP 2021-541558, JPO Type 1 Office Action, mailed Aug. 29, 2023.

* cited by examiner

COMBINED SHOCKWAVE AND ULTRASOUND SOURCE

CROSS-REFERENCE TO RELATED APPLICATIONS

This application is a continuation of pending International Application No. PCT/EP2020/051146 filed on 17 Jan. 2020, which designates the United States and claims priority from European Application No. 19152500.5 filed on 18 Jan. 2019. The disclosure of each of the above-identified applications is incorporated herein by reference.

BACKGROUND

1. Field of the Invention

The invention relates to method and device configured to generate acoustic shockwaves together with ultrasound waves. The generated waves may be used to fragment stones in human or animal bodies.

2. Description of Relevant Art

A shockwave source is disclosed in U.S. Pat. No. 5,058,569. A coil is mounted on a cylindrical support. When a high-voltage pulse is applied to the coil, further causing a high-current flow in a surrounding cylindrical membrane, the cylindrical membrane expands in radial direction causing a cylindrical pressure wave in the medium surrounding the coil. Such a medium preferably is a liquid such as water. The generated cylindrically-shaped pressure wave is deflected and focused by a paraboloidal reflector to a focus point in an axial direction of the coil. On its way to the focal area and due to superposition in the focal area, the pressure wave steepens up and becomes a shock wave.

In EP 1 651 120 B1, a shockwave-generating system comprising two shockwave generators is disclosed.

In general, all the shockwave devices can break large stones into smaller particles. Ultrasound devices are able to further reduce the particle size. Therefore, a combined treatment with shockwaves and ultrasound leads to significantly better results than the treatment with either shockwaves or ultrasound alone. In practice, it is difficult to apply a treatment with shockwave source first, and then remove the shockwave source and apply an output from the ultrasound source in a next step. This is too complex and time-consuming. Furthermore, between the two steps the smaller particles of a target stone generated by the shockwave drift away from the focus spot, such that focusing a wave on the individual separated particles is very difficult.

EP 2 529 678 B1 discloses a shockwave apparatus comprising two coaxially-arranged shockwave sources. A first shockwave source is driven by a coil, while a second shockwave source is a ballistic shockwave source.

EP1651120 discloses two coaxially arranged shockwave sources.

This combined solution allows the treatment with two different signals at the same time or immediately after each other, which leads to a significant reduction of particle size.

A disadvantage of this proposed solution is that the center of the coil is occupied by a second source and therefore cannot be used for an ultrasound, or x-ray localization device. Therefore, an off-axis location device has to be used, which makes the whole lithotripter more complex and difficult to use.

Further disadvantage is that the penetration depth of a radial pressure wave is significantly smaller as compared to that achieved by focusing of a shock wave produced by an electromagnetic shock wave source.

SUMMARY

The problem to be solved by the invention is to further reduce the size of the remaining stone particles as compared to that achieved by existing devices while reducing damage of body tissue and, specifically, hematoma. A further task is to provide a solution that allows the use of an on-axis ultrasound location device. Yet another object is to keep the source as simple as possible.

Long-term tests have shown that a combined shockwave and ultrasound source (that is a source, combining shockwave and ultrasound capabilities) provides significantly better results as compared to dual-shockwave sources. The particle size can further be reduced in shorter time.

A combined shockwave and ultrasound source includes a transducer connected to a power generator. The transducer may further include a coil and a reflector. The coil has preferably a cylindrical shape and a center axis. The coil may be mounted with its center axis at the center axis of a concave reflector, which preferably has a rotationally symmetric design (for example, the reflector may have a shape of rotational paraboloid). In a related case, a transducer may include a flat coil mounted and/or otherwise arranged under an acoustic lens. Preferably, the coil is covered by a membrane.

A power generator connected to the transducer is configured to generate a high-power signal. When such a high-power signal is applied to the transducer, the transducer produces a wave, guided, reflected or directed to a focal area. If the transducer includes a cylindrical coil, the cylindrical coil generates a cylindrical wave that propagates in a radial direction of the coil and that is preferably symmetrical to the center axis. This wave is reflected by the reflector towards the focal area, which also may be a focal point or focus. Preferably, the focal area is located on the center axis and distant from the coil. The distance separating the focal area from the coil may be in a range between 2 cm and 25 cm depending on the design of the reflector and the coil to leave sufficient space for positioning a patient subject to treatment such as to have a target stone in the patient disintegrated.

The power generator preferably provides a signal in the ultrasound range, for example at a frequency from 20 kHz to 1 MHz. This signal may be a continuous signal or it may include at least one burst or pulse with a duration in a range from about 10 ms to about 100 s, most preferably in a range from about 100 ms to about 5 s. The ultrasound signal has an amplitude specifically adapted to the coil, such that a power in a range from about 1 W to about 1 kW is coupled into the coil. The ultrasound signal may be provided substantially at the same time with and overlap the shockwave signals or, alternatively or in addition, between the shockwave signals. The ultrasound signal may even be configured to completely fill the gap between the shockwave pulses.

The power generator may further generate a shockwave signal that includes one or a plurality of high-voltage pulses having a voltage in a range from about 100 V to about 25 kV, preferably from about 1 kV to about 10 kV, and having a duration in a range from about 10 ns to about 10 ms.

The combination of a power generator for generating an ultrasound signal and a shockwave signal with a transducer containing a coil offers many practical benefits. Basically, a coil can easily be adapted to the generator, for example simply by varying the number of windings and the cross section of the wire. Therefore, inductance and resistance parameters can easily be varied over multiple order of magnitudes, thereby addressing a preferred need for the coil to have an inductance low enough to allow flowing fast rising currents for the shockwave signals. Alternatively or in addition, there may also be two independent coils or a coil with at least one tap adapted to shock waves production and another adapted to ultrasound production. This cannot be achieved with piezo transducers. In general, in embodiments of the invention coil transducers may have a lower impedance level than piezo transducers, which further simplifies the power generator circuit. In addition, coil transducers in the above-mentioned embodiments may provide a significant higher output power than piezo transducers.

With simple, conventionally-structured shock wave generators or ultra-sound generators, the design of a power generator circuit is substantially routine, but the requirements to combine these signals, which largely differ in their electrical characteristics, in the same device multiplies the design problems and makes a combined generator extremely complex. In the present embodiments, the use of coil transducers helps to simplify the generator circuit due to the flexibility in design and adaptability of coils.

Preferably, the shockwave and the ultrasound signal are not applied simultaneously to the coil, that is at a given moment of time there is either a shockwave or an ultrasound signal applied.

A control unit may be provided to control the combined shockwave and ultrasound generator and to provide the timing and preferably the signal amplitude of the power output to the coil that generates shockwave or ultrasound waves.

In an embodiment of a combined shockwave-ultrasound generator, the sub-portions (constituent ultrasound generator circuitry portion and shockwave generator circuitry portion) are combined with a combiner to feed a single coil. Here, an ultrasound generator portion is provided and configured to generate an ultrasound signal and a shockwave generator portion is provided and configured to generate a shockwave signal. The ultrasound signal and the shockwave signal are coupled at a combiner unit, which in turn leads the signals to the coil. The combiner either includes an amplifier to amplify the signals, or provides a circuit configured to isolate the ultrasound generator from the shockwave generator and vice versa, such that a shockwave signal from a shockwave generator does not disturb or destroy the ultrasound generator, and vice versa. The combiner may include at least one switch or a filtering network, which may provide a frequency selective coupling.

A control unit may be provided to control the ultrasound generator and/or the shockwave generator as well as the combiner.

In another related embodiment, the coil is connected to an ultrasound generator. Furthermore, an auxiliary coil is provided and connected to a shockwave generator. Preferably, both coils are arranged coaxially, and most preferably they are held by or at the same coil carrier. Although this embodiment requires a somewhat more complex coil, the ultrasound generator and the shockwave generator may be electrically insulated from each other, which simplifies the circuit design significantly.

BRIEF DESCRIPTION OF THE DRAWINGS

In the following, the invention will be described by way of example, without limitation of the general inventive concept, on examples of embodiment and with reference to the drawings.

Figure 1:
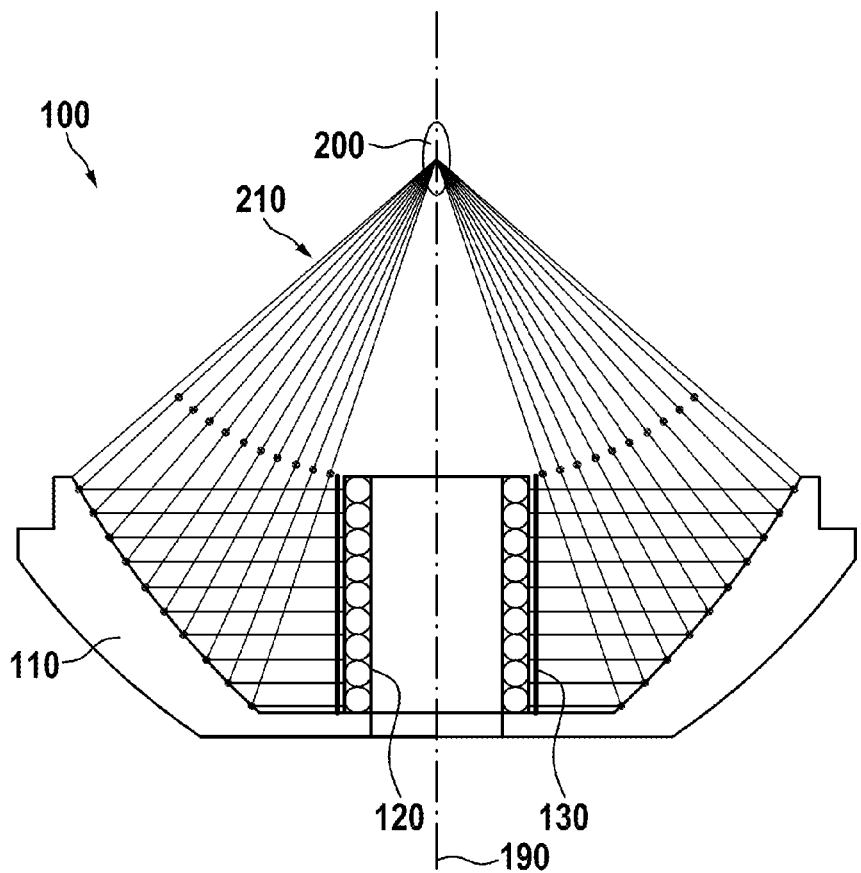
FIG. 1 shows a sectional view of an embodiment.

Generally, the drawings are not to scale. Like elements and components are referred to by like labels and numerals. For the simplicity of illustrations, not all elements and components depicted and labeled in one drawing are necessarily labels in another drawing even if these elements and components appear in such other drawing.

While various modifications and alternative forms, of implementation of the idea of the invention, are within the scope of the invention, specific examples of embodiments are illustrated in the drawings and are described below in detail. It should be understood, however, that the drawings and related detailed description are not intended to limit the implementation of the idea of the invention to the particular form disclosed in this application, but on the contrary, the intention is to cover all modifications, equivalents and alternatives falling within the spirit and scope of the present invention as defined by the appended claims.

DETAILED DESCRIPTION

In FIG. 1, a sectional view of an embodiment is shown. A shockwave and ultrasound source 100 includes a coil 120 surrounded by a cylindrical membrane 130 held within a concave reflector 110. In one example, as shown, the coil with the membrane and the reflector preferably are rotationally symmetrical and have a common center axis 190, as shown. The coil preferably has a cylindrical shape, which may in one case be defined by a cylindrical body on which the windings of a conductive wire are held. Alternatively, the coil may be a flat coil with a flat membrane in front of it. The reflector preferably has a paraboloidal shape such that a cylindrical wave generated by the cylindrical membrane 130 is deflected to a focal area 200, which preferably is located on the common center axis 190 (that is, the center axis of the reflector and the center axis of the coil/membrane substantially coincide; or the center axis of the coil/membrane is located at the center axis of the reflector). FIG. 1 symbolizes the wave propagation 210 from the coil to the focal area. The reflector may be optimized such that a specific required shape of a focal area is obtained. A preferred focal area may be dimensioned as a comparatively small focal point, preferably having a diameter of 10 mm or less. In this embodiment, the coil has a hollow shape thus leaving space inside the coil for an ultrasound location device or any other location device.

Figure 2:
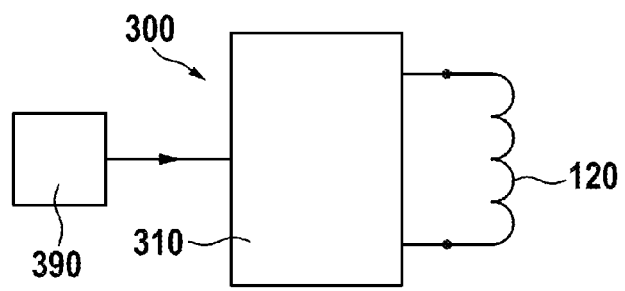
FIG. 2 shows a basic electrical schematic diagram.

In FIG. 2, a basic electrical schematic diagram is shown. The coil 120 is connected to a signal generator 300. This signal generator 300 may include a combined shockwave and ultrasound generator 310, which further may be controlled by a control unit 390. The combined shockwave and ultrasound generator generates signals with a suitable signal shape, frequency, and power to operate the coil such that the coil generates shockwaves and ultrasound waves. The voltage for shockwaves may be in a range from about 100 V to about 25 kV, preferably from about 1 kV to about 10 kV, and having a duration in a range from about 10 ns to about 10 ms. The frequency for ultrasound may be in an ultrasound range from about 20 kHz to about 1 MHz. This signal may be a continuous signal with a duration within a range from about 10 ms to about 100 s, most preferably in a range from about 100 ms to about 5 s. The ultrasound signal has an amplitude the value of which is adapted to the coil, such that a power in a range from about 1 W to about 1 kW is coupled into the coil. The ultrasound signal may be provided at the same time with the shockwave signals or between the shockwave signals, such signal may be configured to even completely fill the gap between shockwave pulses.

Figure 3:
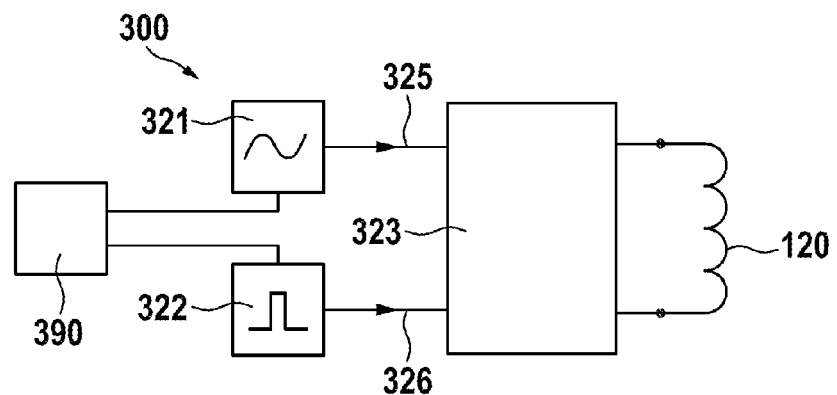
FIG. 3 shows an embodiment with separated ultrasound and shockwave generators.

In FIG. 3, an embodiment with separated ultrasound and shockwave generators is shown. An ultrasound generator 321 generates a wave form or signal 325 corresponding to the ultrasound waves later generated by the coil 120. A shockwave generator 322 generates a shockwave signal 326 corresponding to the shockwaves which are later generated by the coil 120. The ultrasound generator 321 and the shockwave generator 322 may be controlled by a control unit 390. The ultrasound signal 325 of ultrasound generator 321 and the shockwave signal 326 of shockwave generator 322 are combined by a combiner unit 323, which further may be controlled by the control unit 390. There may be two different embodiments of the combiner. In a first embodiment, the ultrasound generator 321 and the shockwave generator 322 only generate low-power signals providing the required wave form. These low-power signals are amplified in the combiner 323 to reach the amplitudes and powers required for the coil 120 to generate the target ultrasound waves and shockwaves. In another embodiment, the ultrasound generator 321 and the shockwave generator 322 provide ultrasound signals 325 and shockwave signals 326 with power(s) sufficient to directly drive the coil 120. In this embodiment, the combiner unit 323 simply combines or merges the signals into a common signal for the coil 120. It is preferred if the combiner electrically insulates the ultrasound generator 321 from the shockwave generator 322 such that, for example, when the shockwave generator 322 generates a shockwave signal, this signal does not damage the ultrasound generator 321, and vice versa. In the simplest embodiment, the combiner 323 may include a switch or a relay configured to switch only one of the sources 321, 322 to the coil 120.

Figure 4:
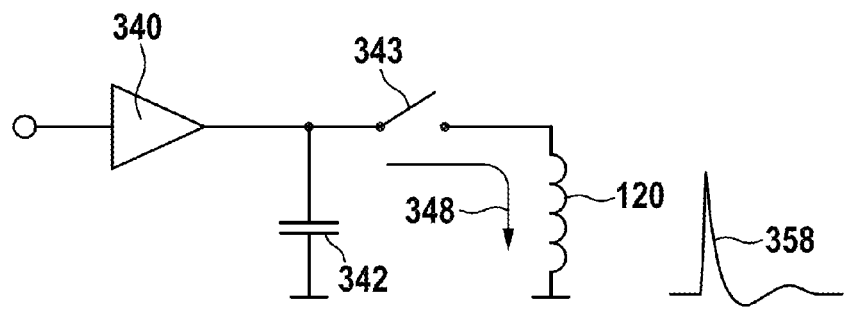
FIG. 4 shows a shockwave generating circuit in more detail.

FIG. 4 illustrates a shockwave-generating circuit in more detail. The circuit includes a high-voltage source 340, a capacitor 342, and a first switch 343. The capacitor 342 is charged by the high-voltage source 340 until the capacitor holds a voltage and therefore energy sufficient for a shockwave pulse. After the charging level is reached, the first switch 343 is closed for a short time such that the capacitor 342 is discharged through coil 120 generating a shockwave pulse. The pulse current is indicated by an arrow 348. The resulting coil current is symbolized by a waveform 358. The closing time preferably is between 20% and 200% of the shockwave pulse duration. In a related embodiment, a diode may be connected in series with the first switch 343 to ensure that current can flow from the capacitor to the coil but not from the coil into the capacitor.

Figure 5:
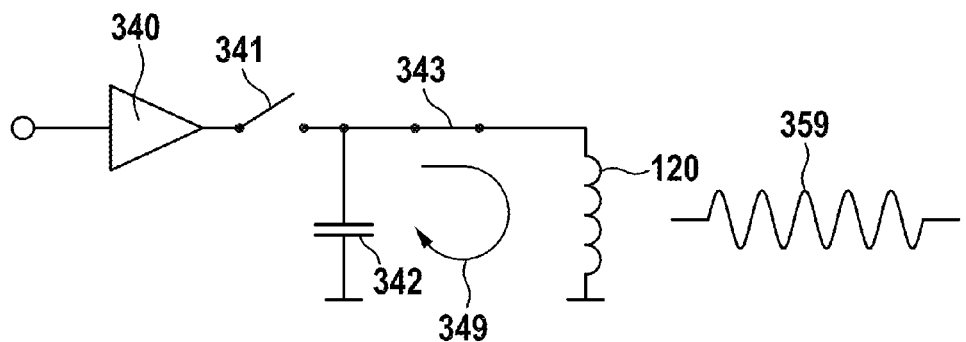
FIG. 5 shows a self-oscillating ultrasound generating circuit in more detail.

FIG. 5 shows a self-oscillating ultrasound-generating circuit in more detail. The circuit includes a high voltage source 340 connected with a second switch 341 to a capacitor 342 and a first switch 343 in series with the coil 120. The capacitor 342 is charged by the high-voltage source 340 until it holds a voltage and therefore energy sufficient for an ultrasound signal. After the charging level is reached, the first switch 343 is closed for the duration of the ultrasound signal, such that the capacitor 342 forms a resonance circuit together with the coil 120 generating an ultrasound signal. The resonant current is indicated by an arrow 349. The resulting coil current is symbolized by a waveform 359. Further, in order to maintain the amplitude of the ultrasound signal, the switch 341 may be repetitively closed to deliver energy needed to compensate for the energy dissipation in the oscillating circuit.

Figure 6:
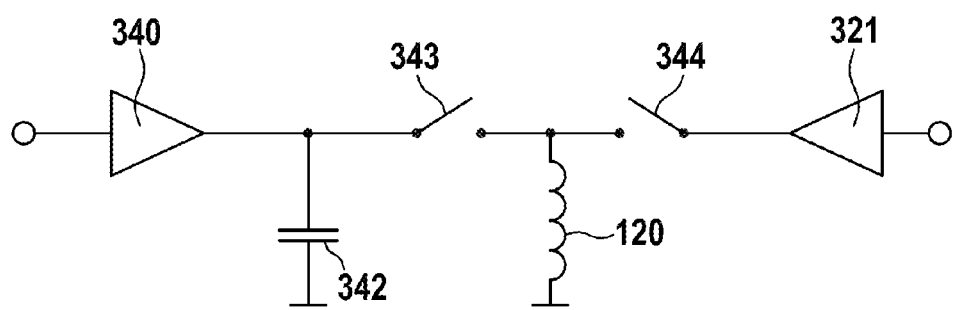
FIG. 6 shows a combined circuit in more detail.

FIG. 6 shows a combined circuit in more detail. The left side of the coil is the same as that of FIG. 4, comprising a high-voltage source 340, a capacitor 342, and a first switch 343. At the right side of the circuit there is an ultrasound generator 321 connected with a third switch 344 to the coil 120. This third switch may be open, if shockwaves has to be generated and it may be closed, if an ultrasound signal has to be generated. An ultrasound signal may be directly coupled from the ultrasound generator 321 into the coil 120. In another embodiment, a resonance circuit with the closed switch 343 formed by the capacitor 342 and the coil 120 may be used to generate the ultrasound signal. The ultrasound generator 321 may be used to provide energy sufficient to compensate for oscillating losses in the circuit. In this latter case, it may be useful to employ an auxiliary switch 341 (shown in FIG. 5) in an open state to isolate the high voltage source 340 from the resonance circuit.

Figure 7:
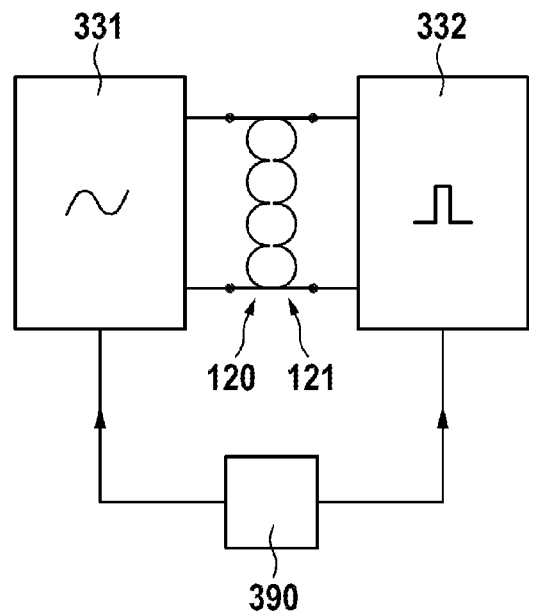
FIG. 7 shows an embodiment with two coils.

FIG. 7 depicts an embodiment with two coils that preferably are inter-leaved. Coil 120 may be connected to an ultrasound generator 331, and an auxiliary coil 121 may be provided that is connected to a shockwave generator 332. Both generators 331, 332 may be controlled by a control circuit 390. It is preferred, if the coil 120 and the auxiliary coil 121 are arranged coaxially with their center axis. Most preferably, the coils 120, 121 are on the same cylindrical base. The optional use of separate coils results in a somewhat more complex mechanical design of the coil assembly, but provides an electrical insulation of the ultrasound generator 331 and the shockwave generator 332.

Figure 8:
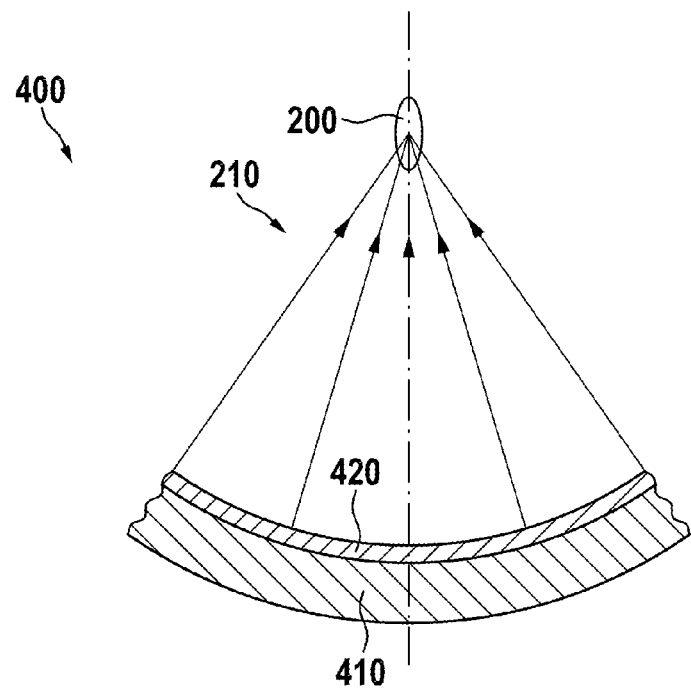
FIG. 8 shows an embodiment of a curved coil transducer.

FIG. 8 shows an embodiment of a curved coil transducer 400. Here, a curved flat coil 420 is held by a body 410 in a sphere-shaped or parabolic arrangement, such that waves generated by the coil 420 are focused into focal area 200. The coil may have a center hole dimensioned for positioning of a localization device therein.

Figure 9:
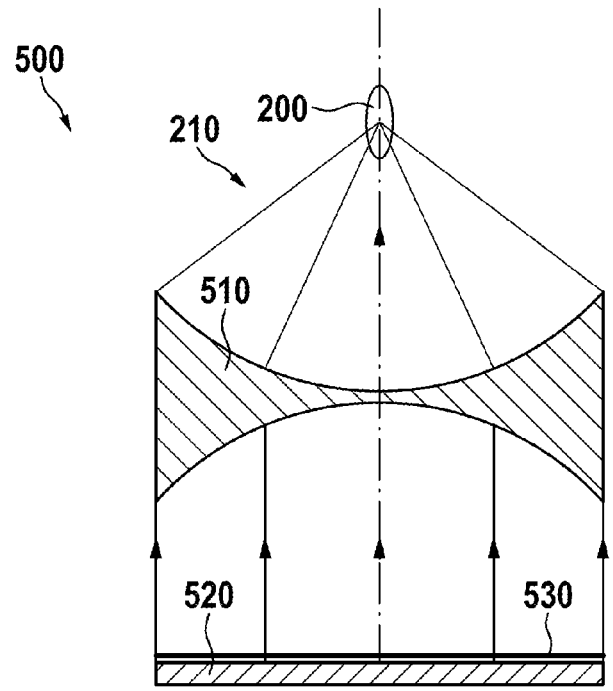
FIG. 9 shows an embodiment of a flat coil transducer.

FIG. 9 shows another flat coil transducer 500, including a flat planar coil 520, a flat membrane 530, and an acoustic lens 510 dimensioned to focus a planar wave generated by the flat planar coil with the flat membrane into the focal area 200.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. In one specific case, when the terms "approximately", "substantially", and "about" are used in reference to a numerical value, these terms represent a range of plus or minus 20% with respect to the specified value, more preferably plus or minus 10%, even more preferably plus or minus 5%, most preferably plus or minus 2% with respect to the specified value.

It will be appreciated to those skilled in the art having the benefit of this disclosure that embodiments of this invention are believed to provide shockwave and ultrasound sources. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 shockwave and ultrasound source
110 reflector
120 coil
121 auxiliary coil
130 cylindrical membrane
190 center axis
200 focal area
210 wave propagation
300 power generator
310 combined shockwave and ultrasound generator
321 ultrasound generator
322 shockwave generator
323 combiner
325 ultrasound signal
326 shockwave signal
331 ultrasound generator
332 shockwave generator
340 high voltage source
341 first switch
342 capacitor
343 second switch
344 third switch
348 pulse current
349 oscillating current
358 shockwave pulse current waveform
359 ultrasound oscillating current waveform
390 control unit
400 curved coil transducer
410 body
420 curved coil
500 flat coil transducer
510 acoustic lens
520 flat planar coil
530 flat membrane

The invention claimed is:

1. An apparatus comprising:
a single transducer configured to generate both an ultrasound wave and a shockwave, the single transducer being connected to a power generator, wherein
the power generator is configured to generate each of a shockwave signal and an ultrasound signals and to provide said ultrasound signal and shockwave signal to the transducer to generate each of the periodic ultrasound wave and the pulse shockwave, and
the single transducer comprises a coil covered by a membrane.

2. The apparatus according to claim 1, wherein the single transducer comprises:
a concave reflector defining a first center axis and
a cylindrical coil with a cylindrical membrane having a second center axis arranged at the first center axis.

3. The apparatus according to claim 1, wherein the single transducer comprises:
a flat coil with a flat membrane arranged under an acoustic lens.

4. The apparatus according to claim 3, wherein the flat coil is a flat planar coil or a flat curved coil.

5. The apparatus according to claim 1, wherein the power generator is configured to alternately generate ultrasound signals and shockwave signals.

6. The apparatus according to claim 1, wherein the power generator comprises an ultrasound generator portion configured to provide an ultrasound signal to the single transducer and a shockwave generator portion configured to provide a shockwave signal to the single transducer, wherein the ultrasound generator portion and the shockwave generator portion are operably coupled via a combiner to the coil.

7. The apparatus according to claim 6, wherein the combiner is a switch.

8. The apparatus according to claim 6, wherein the combiner comprises a power amplifier.

9. The apparatus according to claim 1, further comprising a control unit configured to control at least the combined shockwave and ultrasound generator device.

10. The apparatus according to claim 1, wherein the power generator is configured to provide an ultrasound signal in the ultrasound range from about 20 kHz to about 1 MHz.

11. The apparatus according to claim 1, wherein the power generator is configured to provide ultrasound signal bursts in a duration range from about 100 ms to about 5 s.

12. The apparatus according to claim 1, wherein the power generator is configured to provide a shockwave signal comprising one or a plurality of high-voltage pulses having a voltage in a range from about 100 V to about 25 kV and having a duration in a range from about 10 ns to about 10 ms.

13. The apparatus according to claim 1, wherein the power generator is configured to provide a shockwave signal comprising one or a plurality of high-voltage pulses having a voltage in a range from about 1 kV to about 10 kV and having a duration in a range from about 10 ns to about 10 ms.

14. The apparatus according to claim 1, wherein the power generator includes an ultrasound generator portion and a shockwave generator portion, and wherein the coil of the single transducer is connected to the ultrasound generator portion, and further comprising an auxiliary coil connected to the shockwave generator portion.

* * * * *